United States Patent
Kawasaki et al.

(10) Patent No.: US 11,759,829 B2
(45) Date of Patent: Sep. 19, 2023

(54) METHOD FOR DECONTAMINATING LOW-TEMPERATURE ARTICLE AND A PASS BOX USED IN SAME

(71) Applicant: AIREX CO., LTD., Aichi (JP)

(72) Inventors: Koji Kawasaki, Aichi (JP); Daisuke Kakuda, Aichi (JP); Jun Masudome, Aichi (JP); Haruka Futamura, Aichi (JP); Yukihiro Yazaki, Aichi (JP); Tsukasa Kitano, Aichi (JP); Zhiqiang Guo, Aichi (JP); Ayumi Ogawa, Aichi (JP)

(73) Assignee: AIREX CO., LTD.

( * ) Notice: Subject to any disclaimer, the term of this patent is extended or adjusted under 35 U.S.C. 154(b) by 0 days.

(21) Appl. No.: 17/442,310

(22) PCT Filed: Mar. 17, 2020

(86) PCT No.: PCT/JP2020/011593
§ 371 (c)(1),
(2) Date: Sep. 23, 2021

(87) PCT Pub. No.: WO2020/196072
PCT Pub. Date: Oct. 1, 2020

(65) Prior Publication Data
US 2022/0152667 A1    May 19, 2022

(30) Foreign Application Priority Data
Mar. 28, 2019    (JP) .................................. 2019-062867

(51) Int. Cl.
*B08B 3/12* (2006.01)
*A61L 2/18* (2006.01)
*B08B 7/02* (2006.01)

(52) U.S. Cl.
CPC ................ *B08B 3/123* (2013.01); *A61L 2/18* (2013.01); *B08B 7/028* (2013.01)

(58) Field of Classification Search
None
See application file for complete search history.

(56) References Cited

U.S. PATENT DOCUMENTS

2013/0199053 A1*   8/2013  Yardimci .................. A61L 2/18
                                                              34/279
2015/0158056 A1    6/2015  Rastegar

FOREIGN PATENT DOCUMENTS

JP    2004268019 A    9/2004
JP    2004537345 A    12/2004
(Continued)

OTHER PUBLICATIONS

Google Patents translation of JP2004537345A, retrieved from https://patents.google.com/patent/JP2004537345A/en?oq=jp+2004537345 on Jan. 19, 2023 (Year: 2023).*

(Continued)

*Primary Examiner* — Eric W Golightly
(74) *Attorney, Agent, or Firm* — Quarles & Brady LLP; Yakov S. Sidorin

(57) ABSTRACT

A method for decontaminating a low-temperature article, the method comprising: an applying step including applying a decontamination agent to external surfaces of a low-temperature article and supplying a mist of decontamination agent to a first external surface of said low-temperature article to form a condensed film of the decontamination agent on said first external surface; and a drying step including ultrasonically vibrating vibration boards disposed on a periphery of the low-temperature article to generate sound flows from board surfaces by an ultrasound in a vertical direction, irradiating with ultrasonic waves the low-temperature article with the decontamination agent applied (Continued)

thereto, subjecting said first external surface of the low-temperature article to ultrasonic vibration and acoustic radiation pressure, supplying dry air to the first external surface and drying said first external surface.

4 Claims, 2 Drawing Sheets

(56) References Cited

FOREIGN PATENT DOCUMENTS

| | | | |
|---|---|---|---|
| JP | 2006198120 | A | 8/2006 |
| JP | 2007502032 | A | 2/2007 |
| JP | 2009526637 | A | 7/2009 |
| JP | 2009195563 | A | 9/2009 |
| JP | 2010519140 | A | 6/2010 |
| JP | 2017506157 | A | 3/2017 |

OTHER PUBLICATIONS

PCT International Search Report, PCT/JP2020/011593, dated Jun. 9, 2020, 9 pages.

* cited by examiner

METHOD FOR DECONTAMINATING LOW-TEMPERATURE ARTICLE AND A PASS BOX USED IN SAME

CROSS-REFERENCE TO RELATED APPLICATIONS

This application represents the US national stage entry from the International Application No. PCT/JP2020/011593, filed on 17 Mar. 2020, that claims priority from the Japanese Patent Application No. JP 2019-062867 filed on Mar. 28, 2019. The disclosure of each of the above-identified patent documents is incorporated by reference herein.

TECHNICAL FIELD

The present invention relates to a method for decontaminating a low-temperature article and, more particularly, to a method for decontaminating a low-temperature article using ultrasonic vibration. Also, the present invention relates to a pass box used in a method for decontaminating a low-temperature article.

BACKGROUND ART

In manufacturing settings for pharmaceutical or food products or in the clinical environment such as operating rooms, the indoor working area must inevitably be kept sterile. Particularly in cases where clean rooms as a working chamber for manufacturing pharmaceutical products are decontaminated, advanced decontamination validation needs to be accomplished in accordance with Good Manufacturing Practice (GMP).

In a small-scale work in such a clean environment, a small chamber is employed as a working chamber, and an isolator is used for an operator to work through a glove or a half-suit from the outside of the chamber. The isolator chamber is provided with an intake and exhaust device for maintaining a sterile state so as to receive no contaminants from the external environment. In addition, a sterile state is intended to be maintained when necessary equipment and articles are conveyed to the inside of an isolator in the sterile state from the external environment.

For example, a small spare chamber for conveying, called as a "pass box", is provided for an article to be conveyed to the inside of the isolator. An operator, when conveying an article to the inside of the isolator, first conveys the article to a pass box. In this case, a carry-in door between the isolator and the pass box is sealed. Subsequently, the carry-in door between the pass box and the external environment is sealed to decontaminate the article together with the inside of the pass box. After the pass box is completely decontaminated and a gas for decontamination or the like is removed, the carry-in door between the isolator and the pass box is opened to convey the article to the inside of the isolator.

In recent years, hydrogen peroxide has widely been used (in the form of a gas or mist) to decontaminate a working chamber such as an isolator and a pass box (hereinafter referred to as a "room to be decontaminated") and articles to be conveyed. Advantageously, hydrogen peroxide has a strong sterilization effect, and is inexpensively available and effectively utilized as an environmentally-friendly decontamination gas that is ultimately decomposed into oxygen and water. The following patent document 1 describes that the decontamination effect by hydrogen peroxide is provided by a condensed film of a hydrogen peroxide solution that condenses on the surface of an object to be decontaminated.

CITATION LIST

Patent Literature

Patent Document 1: JP-A-61-004543

SUMMARY OF THE INVENTION

Technical Problem

However, articles to be conveyed to the inside of an isolator by decontamination in a pass box include small containers (incl. vials) for accommodating thermally unstable pharmaceutical products and freeze-dried pharmaceutical products and cells provided for regenerative medicine, and these articles are conveyed to the pass box in cooled or frozen state (generally, about −140° C. to 10° C.) for decontamination.

When these low-temperature articles are to be decontaminated, a gas, fog or mist of a decontamination agent is supplied to allow a decontamination agent to rapidly be condensed on the surface of the low-temperature articles. However, a lower surface temperature of such low-temperature articles unfortunately leads to slower decontamination and inevitable long-time decontamination operation. Meanwhile, the decontamination approach is problematic in that the temperature of the low-temperature article is essentially returned to normal temperature before the article is conveyed to a sterile space such as an isolator by decontamination in a pass box, and long-time decontamination operation is required both in operational efficiency and stability of pharmaceutical products.

Thus, the present invention was made in view of the situation to solve the problems, and has an object to provide a method for decontaminating a low-temperature article capable of accomplishing an effect of decontaminating the surface of a low-temperature article, and reducing the duration of operations to achieve more efficient decontamination works, and a pass box used therein.

Solution to the Problem

To solve the aforementioned problem, inventors of the present invention have carried out an extended investigation to find that a condensed film of a decontamination agent condensed on the surface of a low-temperature article is efficiently dried using ultrasonic irradiation. Based on that technique, the present invention was accomplished.

Specifically, a method for decontaminating a low-temperature article according to the present invention, according to description in claim 1, includes:
  an applying step for applying a decontamination agent to external surfaces of a low-temperature article (40); and
  a drying step for irradiating with ultrasonic waves the low-temperature article applied with the decontamination agent and drying the surface.

Moreover, the present invention is, according to description in claim 2, the method for decontaminating a low-temperature article according to claim 1, characterized in that
  in the drying step, dry air is supplied to the surface of the low-temperature article.

Furthermore, the present invention is, according to description in claim 3, the method for decontaminating a low-temperature article according to claim 1 or 2, characterized in that in the applying step, a decontamination agent mist (31) is supplied to the surface of the low-temperature article to form a condensed film of a decontamination agent on the surface of the low-temperature article.

Moreover, the present invention is, according to description in claim 4, the method for decontaminating a low-temperature article according to claim 3, characterized in that in the drying step, vibration boards (21, 22) disposed on the periphery of the low-temperature article are ultrasonically vibrated to generate sound flows from board surfaces (21a, 22a) by an ultrasound in the vertical direction, and the condensed film of the decontamination agent on the surface of the low-temperature article is subjected to ultrasonic vibration and acoustic radiation pressure.

Furthermore, a pass box according to the present invention is a pass box used in the method for decontaminating a low-temperature article according to any one of claims 1 to 4, including a working chamber (10) for decontaminating a low-temperature article (40), a decontamination agent supply means (30), a dry air supply means (60), and an ultrasound vibration means (21, 22), characterized in that the decontamination agent supply means supplies a decontamination agent to the inside of the working chamber that accommodates the low-temperature article in the state of a decontamination agent mist (31), the dry air supply means supplies dry air to the surface of the low-temperature article, the ultrasound vibration means includes vibration boards (21, 22) disposed adjacent to internal wall surfaces of the working chamber, and the vibration boards are ultrasonically vibrated to generate sound flows from board surfaces (21a, 22a) by an ultrasound in the vertical direction, and the dry air and the sound flows on the low-temperature article in the working chamber are allowed to dry the condensed film of the decontamination agent formed on the surface of the low-temperature article.

Advantageous Effects of Invention

According to the above configuration, the method for decontaminating a low-temperature article according to the present invention includes an applying step and a drying step. The applying step applies a decontamination agent to external surfaces of a low-temperature article. The drying step irradiates with ultrasonic waves the low-temperature article applied with the decontamination agent and dries the surface. Accordingly, the present invention can provide a method for decontaminating a low-temperature article capable of accomplishing an effect of decontaminating the surface of a low-temperature article, and reducing the duration of operations to achieve more efficient decontamination works.

According to the above configuration, in the drying step, dry air is supplied to the surface of the low-temperature article. Accordingly, the above operational advantage can more specifically be provided.

According to the above configuration, in the applying step, a gas, fog or mist of a decontamination agent is supplied to the surface of the low-temperature article. Consequently, a condensed film of the decontamination agent is formed on the surface of the low-temperature article. Accordingly, the above operational advantage can more specifically be provided.

According to the above configuration, in the drying step, vibration boards disposed on the periphery of the low-temperature article are subjected to ultrasonic vibration. Ultrasonic vibration of the vibration boards generates sound flows from board surfaces thereof by an ultrasound in the vertical direction. Then the condensed film of the decontamination agent on the surface of the low-temperature article is subjected to ultrasonic vibration and acoustic radiation pressure. Accordingly, the above operational advantage can more specifically be provided.

According to the above configuration, the pass box according to the present invention includes a working chamber, a decontamination agent supply means, a dry air supply means, and an ultrasound vibration means. The decontamination agent supply means supplies a decontamination agent to the inside of the working chamber that accommodates the low-temperature article in the state of a decontamination agent mist. The dry air supply means supplies dry air to the surface of the low-temperature. The ultrasound vibration means includes vibration boards disposed adjacent to internal wall surfaces of the working chamber, and the vibration boards are ultrasonically vibrated to generate sound flows from board surfaces by an ultrasound in the vertical direction. Accordingly, the dry air and the sound flows on the low-temperature article in the working chamber are allowed to dry the condensed film of the decontamination agent formed on the surface of the low-temperature article. Accordingly, the present invention can provide a pass box capable of accomplishing an effect of decontaminating the surface of a low-temperature article, and reducing the duration of operations to achieve more efficient decontamination works.

DETAILED DESCRIPTION

The method for decontaminating a low-temperature article according to the present invention and a pass box used therein will be described with reference to an embodiment. The present invention is not restricted to the following embodiment.

Figures 1A, 1B:
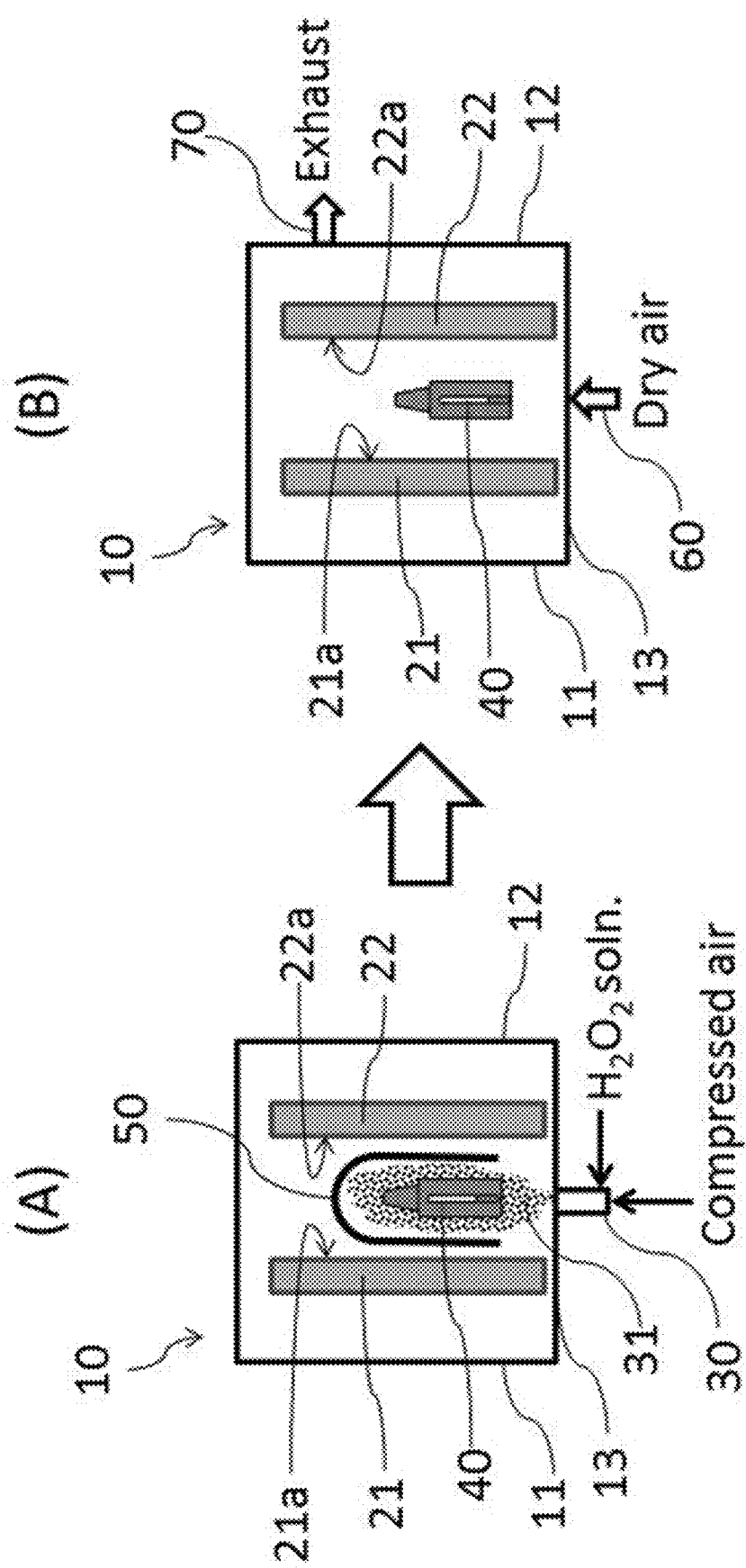
FIG. 1A shows the state in an applying step and FIG. 1B shows the state in a drying step, each outlining the inside of a pass box used in a method for decontaminating a low-temperature article according to this embodiment.

In this embodiment, the method for decontaminating a low-temperature article is performed by an applying step for applying a decontamination agent to external surfaces of a low-temperature article to be decontaminated, and a drying step for irradiating with ultrasonic waves the low-temperature article applied with the decontamination agent and drying the surface. FIG. 1(A) shows the state in an applying step and FIG. 1(B) shows the state in a drying step, each outlining the inside of the pass box used in the method for decontaminating a low-temperature article according to this embodiment.

<Applying Step>

First, an applying step will be described. In FIG. 1(A), a pass box 10 is a stainless housing that is linked to an isolator (not shown) through an opening/closing door (inner door) on a wall surface thereof, the isolator including an opening/closing door (outer door) on other wall surface, leading to the external environment. The linking state between the pass box 10 and the isolator and the structure of opening/closing doors are not particularly restricted, and the pass box is the same as conventional pass boxes in structure. The position of the pass box relative to the isolator is not restricted to that on a side wall surface, and the pass box may be linked to a top wall surface or a bottom wall surface. FIG. 1 shows no inner door, outer door, air supply and exhaust device, or the like.

In FIGS. 1A, 1B, an article 50 that is conveyed from the external environment to the inside of the isolator is conveyed to a center inside the pass box 10. In FIG. 1A, a glass cover 50 covers the low-temperature article 40 from an upper portion to a side lower portion thereof. The cover 50 is provided such that a decontamination agent mist supplied from a decontamination agent supply means (later-described) concentrates around external surfaces of the low-temperature article 40. The cover 50 may be provided in the applying step as needed.

Figure 2:
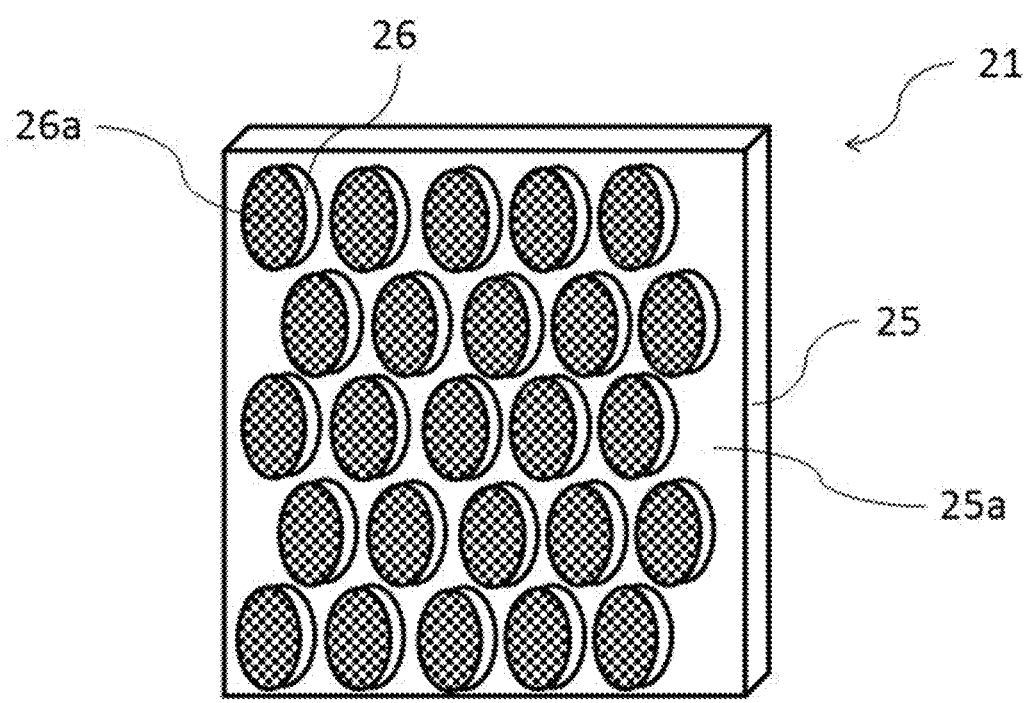
FIG. 2 is a schematic perspective view showing a plurality of ultrasonic speakers arranged in a speaker base in a vibration board included in the pass box in FIG. 1.

In this embodiment, the low-temperature article 40 is to be decontaminated, and a freeze-dried vial. The low-temperature article 40 is conveyed to the inside of an isolator after decontamination inside the pass box 10. In FIG. 1A, 2 vibration boards 21, 22 are disposed inside the pass box 10 as an ultrasound vibration means. These vibration boards 21, 22 are not operated in the applying step, and mentioned in a later-described drying step.

Then, a decontamination agent supply means will be described. In this embodiment, the decontamination agent supply means used is a two-fluid spray nozzle 30, which is placed on a bottom wall surface 13 of the pass box 10 (see FIG. 1A). In this embodiment, the decontamination agent used is a hydrogen peroxide solution ($H_2O_2$ solution). The decontamination agent is not restricted to a hydrogen peroxide solution, and any decontamination agent may be used so long as it is liquid.

The two-fluid spray nozzle 30 converts a hydrogen peroxide solution into a hydrogen peroxide solution mist 31 by compressed air from a compressor (not shown) to supply the same to the inside of the pass box 10. In the present invention, the mist supply device is not restricted to a two-fluid spray nozzle, and a mist generation mechanism and output are not particularly restricted. In FIG. 1A, the hydrogen peroxide solution mist 31 generated from the two-fluid spray nozzle 30 is supplied to the inside of the cover 50 to concentrate on the periphery of the low-temperature article 40. Herein, the hydrogen peroxide solution mist 31 is cooled at a low surface temperature of the low-temperature article 40, and condensed on the surface of the low-temperature article 40 to form a condensed film.

In this embodiment, a decontamination agent mist is employed in the applying step. However, the method for applying a decontamination agent to external surfaces of a low-temperature article in the present invention is not restricted to the supply of a decontamination agent mist using a two-fluid spray nozzle or the like. For example, a low-temperature article with a condensed film formed on the surface may be conveyed to the inside of a pass box after a decontamination agent is applied using a hand spray or the like beforehand. The low-temperature article may be immersed in a decontamination agent aqueous solution adjusted to have a predetermined concentration, and the low-temperature article with a condensed film formed on the surface may be conveyed to the inside of the pass box.

The term "a decontamination agent mist employed in this embodiment" is broadly interpreted and defined as the state of a liquid droplet of a decontamination agent miniaturized or reduced in size and floating in the air, the state of a gas and a liquid agent of a decontamination agent in mixture, and the state of the decontamination agent to repeat the change in phase between condensation and evaporation of a gas and a droplet, and the like. In terms of particle size as well, the mist is also broadly interpreted to include mists, fogs, and liquid droplets, which can be subclassified.

Accordingly, the mist according to the present invention is categorized into a "mist" (the size may be defined as 10 μm or less) or a "fog" (the size may be defined as 5 μm or less), and a mist having a larger particle size. In the present invention, condensation for a mist is time-consuming, and such a mist contains a decontamination agent gas as well.

<Drying Step>

Then, a drying step will be described. In FIG. 1B, a low-temperature article 40 with a condensed film of a hydrogen peroxide solution formed on the surface in the applying step is accommodated inside the pass box 10. A cover 50 covering the low-temperature article 40 is removed. Also, 2 vibration boards 21, 22 are disposed so as to sandwich the low-temperature article 40 on right and left sides. The 2 vibration boards 21, 22 are disposed inside 4 side walls of the pass box 10 against side wall surfaces 11, 12 that are opposite such that vibration surfaces 21a, 22a face horizontally inside the pass box 10. These 2 vibration boards 21, 22 are arranged by allowing board surfaces (vibration surfaces 21a, 22a) thereof to be opposite each other, and the low-temperature article 40 is disposed at the central portion.

Herein, the vibration board 21 will be described (also applied to the vibration board 22). FIG. 2 is a schematic perspective view showing a plurality of ultrasonic speakers arranged in a speaker base in a vibration board included in the pass box in FIG. 1. In FIG. 2, the vibration board 21 includes a base and a plurality of transmitters. In this embodiment, the base used is a speaker base 25, and the transmitter used is an ultrasonic speaker 26. In this embodiment, 25 ultrasonic speakers 26 are arranged on a planar surface 25a of the speaker base 25 so as to be uniform in transmission direction of a vibration surface 26a (leftward as seen from the front shown). The number of ultrasonic speakers is not particularly restricted.

In this embodiment, the ultrasonic speaker 26 used is an ultradirectional ultrasonic speaker. Specifically, an ultrasonic speaker (DC12V, 50 mA) of frequency modulation system for transmitting an ultrasound whose frequency is around 40 KHz is used. The type, size, structure and output of the ultrasonic speaker are not particularly restricted. In the present invention, the vibration board included in the mist control device is not restricted to an ultrasonic speaker, and the ultrasonic generation mechanism, frequency range and output are not particularly restricted.

In this embodiment, a plurality of (25) ultrasonic speakers 26 are arranged so as to be uniform in transmission direction of the vibration surface 46a, and the transmitters are operated in the same phase to mutually amplify ultrasounds from the plurality of ultrasonic speakers 46 in the front direction and mutually cancel out ultrasounds from the plurality of ultrasonic speakers 46 in the lateral direction. Consequently, the ultrasonic speakers 26 arranged on the speaker base 25 are ultrasonically vibrated to generate a significantly directional sound flow traveling in the air from each of the vibration surfaces 26a in the vertical direction. The frequency and output of the ultrasonic speakers 26 are controlled by an ultrasonic controller (not shown) to achieve efficient decontamination operations.

In FIG. 1B, an intake pipe 60 and an exhaust device 70 are provided. The intake pipe 60 is provided on the bottom wall surface 13 of the pass box 10 to supply dry air to the inside of the pass box 10. Other dry gas such as nitrogen gas may be supplied in place of dry air. The exhaust device 70 is provided on the side wall surface 12 of the pass box 10 to discharge wet air generated by drying inside the pass box 10 and an evaporated decontamination agent gas to the outside. In FIG. 1B, the two-fluid spray nozzle 30 is not operated, and it is not described.

The supply of dry air from the intake pipe 60 in this state and ultrasonic vibration of the ultrasonic speaker 26 of each vibration board generate significantly directional sound flows traveling in the vertical direction from 2 vibration surfaces 21a, 22a. These sound flows generate pressing forces by ultrasonic vibration and acoustic radiation pressure on the surface of the low-temperature article 40. Accordingly, a condensed film of a hydrogen peroxide solution condensed on the low-temperature article 40 is vibrated, and the condensed film is dried by the action of dry air and condensation of the hydrogen peroxide solution is promoted, resulting in higher decontamination effects by oxidation.

Subsequently, using the pass box 10 according to this embodiment by reference to an example, the method for decontaminating a low-temperature article according to the present invention will specifically be described. The present invention is not restricted to the following example.

EXAMPLE

In this example, an operation of decontaminating external surfaces of a freeze-dried vial (surface temperature: 0° C., contents: 5 ml of distilled water) in a pass box and conveying it to the inside of an isolator was performed. The vial used is made of polyethylene with the dimensions of 7 cm in height, 2 cm in diameter and 15 ml in volume.

Decontamination effects on external surfaces of the freeze-dried vial were confirmed by an enzyme indicator (EI). EI is an apparatus for fluorescence assay of residual enzymatic activity after a test to confirm decontamination effects, and this approach is advantageous in removing culture operations in conventional biological indicator (BI) and reducing the duration of operations. EI's comparative equality with BI was recently confirmed and the EI technique has proactively been used. The log spore reduction (LRD) value was calculated by the logarithmic decrement of fungi from the EI's fluorescence intensity after decontamination, and the LRD of 4 to 6 or more was judged as a sufficiently acceptable decontamination standard effect inside the pass box.

In this example, a pass box 10 of FIGS. 1A, 1B was used. A pass box 10 disposed is 0.0022 $m^3$ in volume (15 cm in length, 12 cm in width, 12 cm in thickness; and internal wall surfaces are stainless plates), including 2 vibration boards 21, 22. There are 4 applying methods in the step for applying hydrogen peroxide: (1) dipping method; (2) hand spray method; (3) mist method (using two-fluid spray nozzle); and (4) fog method (using ultrasonic humidifier: nebulizer). In the (3) mist method and (4) fog method, a hydrogen peroxide solution (35 W/V %) was used for spraying. On the other hand, in the (1) dipping method and (2) hand spray method, a 6 W/V %-diluted hydrogen peroxide solution was used.

Table 1 shows the amount of generation, applying time, and total applying amount in the step for applying hydrogen peroxide, and air flow amount and drying time in the drying step. In the applying step, the total applying amount by the (1) dipping method could not be measured. Also, in the drying step, drying for the (2) hand spray method was performed by increasing the air flow amount. Table 1 shows the LRD values and temperature rise of vials decontaminated under these conditions.

TABLE 1

| Applying method | $H_2O_2$ applying step | | | Drying step | | Results | |
| --- | --- | --- | --- | --- | --- | --- | --- |
| | Amount of generation (g/min) | Applying time (sec) | Total applying amount (g) | Air flow amount (L/min) | Drying time (min) | LRD value | Temperature rise (ΔT) |
| (1) Dipping method | — | 5 | — | 150 | 5 | >9.0 | — |
| (2) Hand spray | — | — | 2.5 | 150 | 5 | 7.9 | +3.0° C. |
| (3) Mist | 2 | 60 | 2.0 | 150 | 5 | >9.0 | +3.0° C. |
| (4) Fog | 2 | 180 | 6.9 | 150 | 5 | <2.5 | +4.0° C. |

As shown in Table 1, the methods other than the (4) fog method all demonstrate favorable LRD values, and sufficient decontamination effects for a short period of time. In the (4) fog method, it is believed that formation of a condensed film on the surface of vials requires much time. The reason for temperature rise on the surface of vials has not clearly been identified, but this is probably because of vibrational energy applied from sound flows. Another reason seems to be prompt oxidation decomposition of a hydrogen peroxide solution. However, it is believed that such a short-time temperature rise doesn't affect the quality of low-temperature articles to be decontaminated.

Accordingly, the supply of a hydrogen peroxide mist or the like to a low-temperature article causes its surface to be a wet area (to form a condensed film). It is found that when the wet area is supplied with dry air and irradiated with sound flows of ultrasonic vibration, evaporation effects are promoted for a short period of time (approx. 3 minutes), and the surface concentration of a hydrogen peroxide solution sharply rises to obtain significant decontamination effects.

The present embodiment can provide a method for decontaminating a low-temperature article capable of accomplishing an effect of decontaminating the surface of a low-temperature article, and reducing the duration of operations to achieve more efficient decontamination works, and a pass box used therein.

The goal of the present invention is achieved not only with the above-described embodiment, but also with the following various alternatives.

(1) In the above embodiment, a two-fluid spray nozzle is used to apply a decontamination agent in an applying step. However, the spray nozzle is not restricted thereto, and an ultrasonic humidifier (nebulizer) used in the example, a hand spray, or a dipping technique in a decontamination liquid may be used.

(2) In the above embodiment, a vibration board used includes a plurality of ultrasonic speakers arranged in a speaker base. However, the vibration board is not restricted thereto, and any type of vibration board may be used so long as it includes a Langevin type transducer fixed to a stainless steel having a constant area or a board surface for ultrasonic vibration.

(3) In the above embodiment, a decontamination agent used is a hydrogen peroxide solution ($H_2O_2$ solution). However, the decontamination agent is not restricted thereto, and it may be any type of decontamination agent so long as it is liquid.

(4) In the above embodiment, 2 vibration boards are arranged on 2 side walls. However, the configuration is not restricted thereto, and 4 vibration boards may be arranged on 4 side walls, or vibration boards may be arranged on 2 to 6 side walls out of 6 side walls including a top wall surface and a bottom wall surface on 4 side walls.

REFERENCE SIGNS LIST

10 . . . Pass box, 11, 12, 13 . . . Wall surface,
21, 22 . . . Vibration board, 21a, 22a . . . Vibration surface,
25 . . . Speaker base, 25a . . . Planar surface of speaker base,
26 . . . Ultrasonic speaker, 26a . . . Vibration surface of ultrasonic speaker,
30 . . . Two-fluid spray nozzle, 31 . . . Hydrogen peroxide solution mist,
40 . . . Low-temperature article, 50 . . . Cover, 60 . . . Intake pipe,
70 . . . Exhaust device.

The invention claimed is:

1. A method for decontaminating a low-temperature article, the method comprising:

an applying step including applying a decontamination agent to external surfaces of a low-temperature article and supplying a mist of decontamination agent to a first external surface of said low-temperature article to form a condensed film of the decontamination agent on said first external surface; and a drying step including ultrasonically vibrating vibration boards disposed on a periphery of the low-temperature article to generate sound flows from board surfaces by an ultrasound in a vertical direction, irradiating with ultrasonic waves the low-temperature article with the decontamination agent applied thereto, subjecting said first external surface of the low-temperature article to ultrasonic vibration and acoustic radiation pressure, supplying dry air to the first external surface and drying said first external surface.

2. A method according to claim 1, wherein:
said supplying the mist of decontamination agent includes supplying said mist to an inside of a working chamber that is configured to accommodate said low-temperature article.

3. A method according to claim 2, wherein the drying step drying directing the dry air in the working chamber to dry the condensed film of the decontamination agent formed on the first external surface of the low-temperature article.

4. A method according to claim 1, wherein said decontaminating the low-temperature article is carried out together with decontaminating an inside of a working chamber configured to accommodate said low-temperature article.

* * * * *